(12) United States Patent
Adorante et al.

(10) Patent No.: US 6,479,458 B1
(45) Date of Patent: Nov. 12, 2002

(54) TARGETING THE REVERSE MODE OF THE $NA^+/CA^{2+}$ EXCHANGER FOR THE TREATMENT OF OPTIC NEUROPATHY ASSOCIATED WITH GLAUCOMA AND ISCHEMIC OPTIC NEUROPATHY

(75) Inventors: Joseph S. Adorante, Irvine, CA (US); George R. Ehring, Huntington Beach, CA (US); Kara L. Kopper, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/005,829

(22) Filed: Nov. 8, 2001

(51) Int. Cl.$^7$ ................................................ A61K 38/00
(52) U.S. Cl. ........................ 514/11; 514/580; 514/585; 514/912
(58) Field of Search ................................ 514/580, 585, 514/11, 912

(56) References Cited

U.S. PATENT DOCUMENTS

| | | | |
|---|---|---|---|
| 5,527,814 A | 6/1996 | Louvel | 514/367 |
| 5,610,184 A | 3/1997 | Shahinian, Jr. | 514/540 |
| 5,922,746 A | 7/1999 | Adorante | 514/373 |

FOREIGN PATENT DOCUMENTS

| | | |
|---|---|---|
| EP | 0 608 604 A1 | 10/1993 |
| EP | 0 659 430 A1 | 12/1994 |
| FR | 2714828 | 1/1994 |

OTHER PUBLICATIONS

Bruce R. Ransom et al, Anoxic Injury of Central Myelinated Axons; New York 1993 Raven Press p. 121 through 151.
Peter K. Stys, et al, Ionic Mechanisms of Anoxic Injury in Mammallian Role ofNa+ Channels and NA+Ca2+ Exchange.
Role of Na+ Conductance and the Na+–Ca++ Exchanger in Anoxic Injury of CNS White Matter S.G. Waxman, et al Stuttgart 1992 p. 13–31.
The Extracellular Patch Clamp: A Method for Resolving Currents Through Indivicual Open Channels in Biological Membrances Neher et al 1978.
Improved Patch–Clamp Techniques for High–Resolution Current Recording from Cells and Cell–Free Membrane Patche O.P. Hamill et al Verlag 1981.
Role of Extracellular Calcium in Anoxic Injury of Mammalian Central White Matter Peter K. Stys et al USA 1990.
Arachidonic Acid Inhibits Sodium Currents and Synaptic Transmission in Cultured Straital Neurons, Douglas D. Fraser Cell Press 1993.
Protective Effects of Antiarrhythmic Agents Against Anoxic Injury in CNS White Matter Peter K. Stys. Ontario, Canada 1994.
Calcium: Still Center–Stage in Hypoxic–Ischemic Neuronal Death Dennis W. Choi USA 1995 p. 58–60.
Interaction Between Exteral Na+ and Mexilentine on Na+ Channel in Guinea–Pig Ventricular Myoctes, Masahiro Ono Japan 1995 p. 101–109.
Textbook of Ocular Pharmacology New York 1997 p. 330–334.
Noninactivating, Tetrodtoxin–Sensitive Na+ Conductance in Rat Optic Nerve Axons Peter Stys p. 6976–6980 USA 1993.

*Primary Examiner*—Zohreh Fay
(74) *Attorney, Agent, or Firm*—Walter A. Hackler

(57) ABSTRACT

A method for preventing retinal ganglion cell depth, associated with glaucoma, in an animal of the mammalian species, including humans, comprising the step of administering to ganglion cells and their axons (optic nerve) of said mammal a pharmaceutical composition which comprises as its active ingredient one or more compounds having activity for blocking a reverse mode of the sodium/calcium exchanger.

20 Claims, 1 Drawing Sheet

NORMAL CONDITIONS
MEMBRANE POTENTIAL = -75 mV

ISCHEMIC CONDITIONS
MEMBRANE POTENTIAL DEPOLARIZED

TARGETING THE REVERSE MODE OF THE NA+/CA2+ EXCHANGER FOR THE TREATMENT OF OPTIC NEUROPATHY ASSOCIATED WITH GLAUCOMA AND ISCHEMIC OPTIC NEUROPATHY

The present invention generally relates to a method for preventing retinal ganglion cell death, associated with glaucoma, and is more specifically directed to administering to retinal ganglion cells of a mammal, a compound which blocks the reverse mode of the sodium/calcium exchanger.

Glaucoma, a disease of unknown etiology, results in the degeneration of the optic nerve and the subsequent loss of the visual field. In the case of primary open angle glaucoma (PAOG) where intraocular pressure is elevated present therapies rely on lowering pressure in the hope that this may retard the progressive loss of the visual field.

Another approach to prevent the loss of nerve fibers associated with glaucoma is to target the retinal ganglion cell or optic nerve directly, see U.S. Pat. No. 5,922,746. It has been shown that a novel class of voltage-gated sodium $Na^+$ channels and the sodium/calcium exchanger ($Na^+/Ca^{2+}$) residing within the optic nerve are responsible for the damage to rat optic nerve following anoxia or hypoxia. The underlying hypothesis is that elevation of intracellular calcium beyond physiological levels kills retinal ganglion cells and their axons. It is believed that during hypoxia or anoxia when intracellular ATP concentrations decrease the following series of intracellular events occur within the optic nerve tract. As a result of the decreased functioning of the Na/K pump, which is fueled by intracellular ATP, intracellular levels of potassium ($K^+$) and $Na^+$ decrease and increase respectively. Subsequent loss of cell $K^+$ results in an increase in extracellular $K^+$ that subsequently depolarizes the optic nerve axons. Depolarization activates voltage-gated $Na^+$ channels including a unique subset of $Na^+$ channels that do not inactivate during prolonged depolarization. $Na^+$ channels that do not inactivate are known as non-inactivating or persistent $Na^+$ channels. Persistent $Na^+$ channels provide a sustained influx of $Na^+$ into anoxic/depolarized optic nerve tract (Stys et al, 1993, Waxman et al, 1992). Sustained $Na^+$ influx and reduced $Na^+/K^+$ pump activity results in an elevated intracellular $Na^+$ concentration, a condition termed "$Na^+$ overload". $Na^+$ overload and membrane depolarization results in the reverse operation of the electrogenic $Na^+/Ca^{2+}$ exchanger, which normally operates to extrude intracellular $Ca^{2+}$. Reverse operation of the $Na^+/Ca^{2+}$ exchanger leads to a large increase in intracellular $Ca^{2+}$ ($Ca^{2+}$ can increase from nanmolar to micromolar levels). Large increases in cell $Ca^{2+}$ are believed to be responsible for neuronal cell death triggered by a variety of insults. As such prevention of $Ca^{2+}$ overload has been demonstrated to be neuroprotective in CNS neurons including rat optic nerve (Stys et al, 1993).

SUMMARY OF THE INVENTION

The present invention is directed to preventing optic nerve malfunction during following ischemia/hypoxia by inhibiting the $Na^+/Ca^{2+}$ exchanger. As mentioned above, under hypoxic/ischemic conditions the exchanger is running in the reverse mode, thus loading the cell with $Ca^{2+}$ (see FIG. 2).

On the other hand, $Na^+/Ca^{2+}$ exchangers of retinal ganglion cells (RGCs), their associated axons (that make up the optic nerve), and other retinal cells, that are not ischemic, depolarized, or overloaded with $Na^+$, will possess $Na^+/Ca^+$ exchangers that are running in the normal forward mode.

Since $Na^+/Ca^{2+}$ exchanger in the forward mode is an important regulator of cell $Na^+/Ca^{2+}$ (Blaustein and Lederer, 1999), keeping it within physiological limits, it would not be prudent to block this mode of the exchanger. Therefore, a inhibitor of the $Na^+/Ca^{2+}$ exchanger that prevents the reverse but not forward mode of transport could spare ischemic/hypoxic retinal ganglion cells that are overloaded with $Na^+$ while allowing relatively healthy cells (that posses exchangers running in the forward mode) to regulate intracellular $Ca^{2+}$.

Recently a compound has been developed that selectively targets the reverse mode of the $Na^+/Ca^{2+}$ exchanger (Iwomoto et al, J. Biological Chem. 271:22391–22397 1996). This compound named KB-R743 ((2-[2-[4-(4-nitorbenzyloxy)phenyl]ethyl]isothiourea methanesulfonte) has been found to preferentially block the reverse mode of the $Na^+/Ca^{2+}$ exchanger in a variety of cell types including neurons (Breder et al, 2000, Iwomoto et al, 1996.). In addition, cyclosporin A as been identified as having made a specific activity in the inhibition of sodium-calcium exchange (Biophysical Journal UCI 80, No. 1, part 2 of 2, January 2001).

Although in glaucoma, the sequence of pathological events leading to the death of RGCs and the optic nerve tract; is not known, it is likely to involve a lethal increase in intracellular $Ca^{2+}$. If, in the optic nerve, this increase in $Ca^{2+}$ is the result of a reversal of $Na^+/Ca^{2+}$ exchanger, subsequent to depolarization and/or $Na^+$ overload (mediated by non-inactivating Na channels) then it should be possible to spare axons and their RGCs by blocking reversal of the $Na^+/Ca^{2+}$ exchanger. Therefore blockade of the reverse mode of the $Na^+/Ca^{2+}$ exchanger may prevent or reduce the loss of optic nerve tract fibers associated with glaucoma.

Accordingly, a method in accordance with the present invention for preventing retinal ganglion cell death associated with glaucoma in an animal of the mammalian species, including humans, includes the steps of administering to the ganglion optic nerve of said manual, a pharmaceutical composition which comprises as its active ingredient, one or more compounds having activity for blocking a reverse mode of the sodium/calcium exchanger.

The invention provides a method for altering a plausible sequence for pathological events in retinal ganglion optic cells associate with glaucoma in order to prevent retinal ganglion cell death. The sequence includes the pathological depolarization of retinal ganglion cells, and influx of millimolar amounts of sodium via non-inactivating the sodium channels and a subsequent reversal of the sodium/calcium exchanger, mediated by both membrane depolarization and increased intracellular sodium causing a toxic buildup of intracellular calcium. Specifically, the method comprises the blocking of a reverse mode of the sodium/calcium exchanger in retinal ganglion cells in order to prevent buildup of the calcium level in the retinal ganglion cells to a lethal level.

In accordance with the present invention, the method is provided for maintaining normal intracellular calcium in ganglion cells following a period of anoxia. The method comprises contacting the ganglion neuronal cells with a composition for blocking of a reverse mode of the sodium/calcium exchanger in the retinal ganglion neuronal cells. Thus, the present invention provides a method for providing a neuroprotective effect to retinal ganglion cells in the eye of the human.

More specifically, the method includes the administration of a pharmaceutical composition comprising ((2-[2-[4-(4-nitorbenzyloxy)phenyl]ethyl]isothiourea methanesulfonte) to an eye. In addition, the method may include the pharmaceutical composition comprising of cyclosporian A and additional compositions and compounds which may be determined by a screen as hereinafter set forth.

BRIEF DESCRIPTION OF THE DRAWINGS

The advantages and features of the present invention would be better understood by the following description when considered in conjunction with the accompanying drawings.

DETAILED DESCRIPTION

Figure 1:
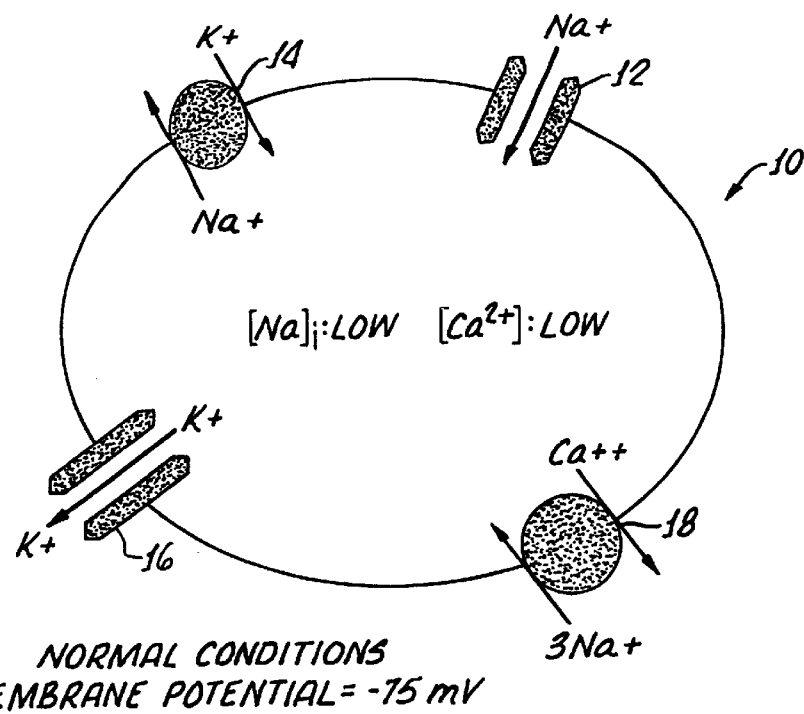
FIG. 1 is a diagram of the assumed relevant transport mechanisms for a retinal ganglion cell under normal conditions.

This approach is unique and novel in that it does not target cellular mechanisms that modulate aqueous humor dynamics and therefore intraocular pressure. Rather, it targets the optic nerve tract which ultimately becomes compromised and is eventually destroyed in glaucoma. Moreover, as mentioned previously, it should be possible to block only the reversed mode of the $Na^+Ca^{2+}$ exchanger without compromising those operating in the forward mode. Thus, the optic nerve can still be protected from $Ca^{2+}$ overload by selectively targeting only those axons (and RGCs) that have their $Na^+/Ca^{2+}$ exchanger running in the reverse mode thereby enabling healthy cells to carrying out the business of regulating and controlling intracellular $Na^+/Ca^{2+}$.

The balance of intracellular concentration is described in co-pending U.S. Ser. No. 09/273,832 filed Mar. 22, 1999 and in U.S. Pat. No. 5,922,746. This application and patent are incorporated herewith in their entirely.

Compositions utilized in accordance with the method of the present invention have activity for blocking the reverse mode of the sodium/calcium exchanger. The inhibitors of the present invention prevent the influx of $Ca^{2+}$ ions into the neuronal cell through the reverse action of the sodium/calcium exchanger.

Pharmaceutically acceptable salts of the compounds can also be used in accordance with the present invention. A pharmaceutically acceptable salt may be any salt which retains the activity of the parent compound and does not impart any deleterious or untoward effect on the subject to which it is administered and in the context in which it is administered.

Such a salt may derive from any organic or inorganic acid or base. The salt may be a mono or polyvalent ion. Of particular interest where the acid function is concerned are the inorganic ions, such as alkali ions, e.g. sodium, potassium, etc. Organic amine salts may be made with amines, particularly ammonium salts such as mono-, di- and trialkyl amines, e.g., alkylamines wherein each alkyl group may comprise up to six carbon atoms, or ethanol amines. Salts may also be formed with caffeine, tromethamine and similar molecules. It is only important that the action of any salt of a sodium/calcium exchange inhibitor utilized in the compositions or methods of this invention be able to preferentially block the reverse mode of $Na^+/Ca^{2+}$ exchange of the retinal ganglion cell.

For protecting against retinal ganglion cell damage in a mammalian eye, and particularly for prevention of retinal ganglion cell loss in humans exposed to a condition that causes optic neuron loss, the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has no long term or permanent detrimental effect on the eye to which it is administered. Examples of opthalmically acceptable carriers include water (distilled or deionized water), saline and other aqueous media. In accordance with the invention, the active compounds are preferably soluble in the carrier which is employed for their administration, so that the active compounds are administered to the eye in the form of a solution. Alternatively, a suspension of the active compound or compounds (or salts thereof) in a suitable carrier may also be employed.

In accordance with the invention, the active compounds (or mixtures or salts thereof) are administered in an ophthalmically acceptable carrier in sufficient concentration so as to deliver an effective amount of the active compound or compounds to the optic nerve site of the eye. Preferably, the ophthalmic, therapeutic solutions contain one or more of the active compounds in a concentration range of approximately 0.0001% to approximately 1% (weight by volume) and more preferably approximately 0.0005% to approximately 0.1% (weight by volume).

Any method of administering drugs to the retinal ganglion cell site of a mammalian eye may be employed to administer, in accordance with the present invention, the active compound or compounds to the eye to be treated. By the term "administering" is meant to include those general systemic drug administration modes, e.g., injection directly into the patient's blood vessels, oral administration and the like, which result in the compound or compounds being systemically available. Also, intercameral injection may be utilized to delver the reverse mode $Na^+/Ca^{2+}$ exchange inhibitor to the retinal ganglion cell site. The primary effect on the mammal resulting from the direct administering of the active compound or compounds to the mammal's eye is the prevention of optic nerve loss. Preferably, the active useful compound or compounds are applied topically to the eye or are injected directly into the eye.

Injection of ophthalmic preparations, for example ocular drops, gels or creams may be used because of ease of application, ease of dose delivery and fewer systemic side effects, for example cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.0001 to about 1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium potassium, chlorobutanol, thimerosal, phynylmercuric acetate, and phenylmercuric nitrate. Likewise, various preferred vehicles may be used in such ophthalmic preparation. These vehicles include, but are not limited to, polyvinal alcohol, povidone, hyproxypropyl methyl cellulose, polyxamers, carboxymethyl cellulose and hydroxyethyl cellulose.

Tonicity adjustors may be added as needed or convenient. They include, but are not limited to, salts, particularly sodium chloride, potassium chloride, etc., mannitol and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acethylcystein, butylated hydroxyanisooe, and butylated bydroxytoluene.

Those skilled in the art will recognize that the frequency of administration depends on the precise nature of the active ingredient and its concentration in the ophthalmic formulation.

Specific examples of reverse mode $Na^+/Ca^2$ inhibitors which are used as the active effective ingredients in the ophthalmic compositions of the present invention are ((2-[2-[4(4-nitorbenzyloxy) phenyl]ethyl]isothieurea methanesulfonate) and cyclosporing A.

Other examples of sodium channel reverse mode $Na^+/Ca^2$ inhibitors which are suitable as the active effective ingredients in the ophthalmic compositions of the present invention are determined in the following screening paradigms:

To find drugs that are efficacious in treating glaucoma it is necessary to have a high throughput screen in place that will distinguish compounds that preferentially block the reverse over the forward mode of the $Na^+/Ca^{2+}$ exchanger. The most efficient way to accomplish this task is to first have the exchanger expressed in an appropriate cell line such as HEK-293 cells. These cells can be then utilized in 96 well plates and loaded with an appropriate calcium-sensitive dye such as FLUO-3. A screening system such as the FLIPR (Molecular Devices) will subsequently be used to simultaneously monitor changes in intracellular $Ca^{2+}$ in all the wells containing the cells with the expressed exchangers.

Two different manipulations will be required of this screen. To look at the effect of a given drug on the reverse mode of the exchanger cells will first be incubated in a physiological Ringer containing ouabain (a sodium pump inhibitor) and an appropriate $Ca^{2+}$ channel blocker for a determined period of time. Following incubation the media is removed and substituted with a $Na^+$-free Ringer (choline may be used as a $Na^+$ substitute). This will cause cell $Ca^{2+}$ to rise as intracellular $Na^+$ exchanges for media $Ca^{2+}$. To test a drug one simply preincubates the cells for a determined period of time at different doses and then performs the above described experimental maneuver. The peak increase in cell $Ca^{2+}$ in the absence of drug can then be compared with drug treated cells and a dose response and $IC_{50}$ value can then be obtained.

To test for a drugs effect on the forward mode of the exchanger cells will be incubated in a $Na^+$-free Ringer containing 1 $\mu M$ thapsigargin and 10 $\mu M$ FCPP. This combination will cause cell $Ca^{2+}$ to rise since $Ca^{2+}$ will be released from cell stores (endopasmic reticulum and mitochondria). Upon addition of $Na^+$ to the media, elevated $Ca^{2+}$ resulting from thapsigargin and FCCP addition will be decreased toward control level as the $Na^+/Ca^{2+}$ exchanger runs in the forward direction extruding cell $Ca^{2+}$ in exchange for media $Na^+$. Here again, to determine a drugs' effect on the forward mode of the exchanger, one simply preincubates the cells with the drug at varying concentration and compares these to drug-free controls. A dose response can then be readily be obtained.

EXAMPLE

FIG. 1 shows a representation of a retinal ganglion cell 10, under normal conditions and assumed relevant transport mechanisms 12, 14, 16, 18 responsible for maintaining the sodium ($Na^+$), potassium ($K^+$) and the calcium ($Ca^{2+}$) gradients and electrical activity of the cell. As shown under normal conditions ATP levels are adequate and furnish the fuel needed to drive the $Na^{+K+}$ pump 14 that maintains the $K^+$ and $Na^+$ gradients, keeping intracellular concentrations of $K^+$ high and $Na^+$ low relative to their respective extracellular concentrations. The voltage-gated $Na^+$ and $K^+$ channels 12, 16 provide the currents that make up the action potential. The electronegenic $Na^+Ca^{2+}$ exchanger 18 keeps cellular $Ca^{2+}$ levels within the physiological range (nanomolar).

Figure 2:
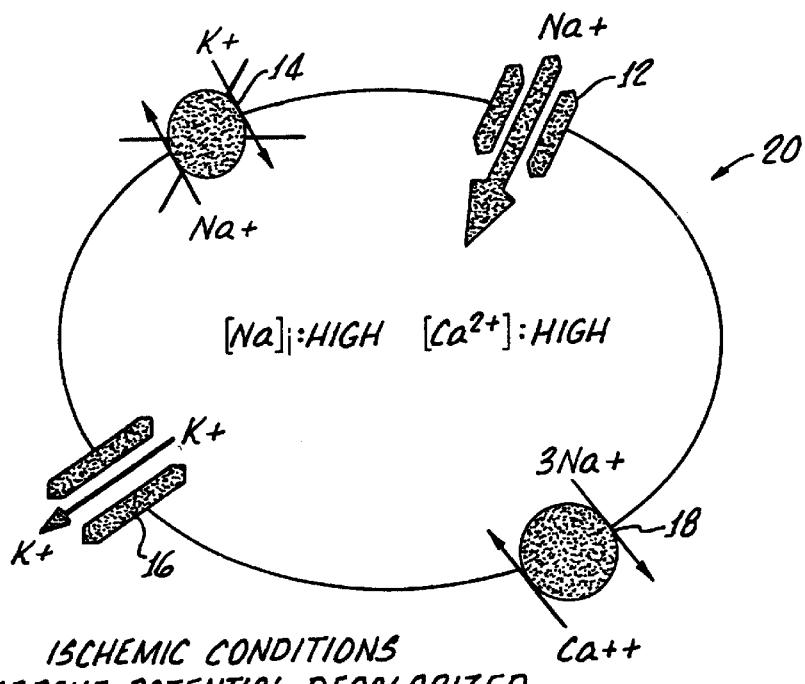
FIG. 2 is a diagram of a retinal ganglion cell under ischemic conditions.

If, however, ATP levels should drop, due to some pathophysiological insult, the axon will depolarize and the $Na^+/K^+$ gradients will collapse over time as a result of $Na^+/K^+$ pump 14 inhibition as shown in FIG. 2 for a cell 20 under ischemic conditions. The rise in cellular $Na^+$ is mediated by a subset of voltage-gated $Na^+$ channels that do not inactivate over time. These $Na^+$ channels are coined "noninactivating". The combination of membrane depolarization and intracellular $Na^+$ increase is sufficient to drive the $Na^+/Ca^{2+}$ exchanger 18 backwards (see FIG. 2) such that the ganglion cells load with lethal levels of $Ca^{2+}$. It is assumed that this scenario occurs in the retinal ganglion cell in glaucoma.

Inhibitors of the reverse mode of the $Na^+/Ca^{2+}$ exchanger prevents loading of the cells with lethal levels of $Ca^{2+}$ In view of the above, it is clear that the scope of the present invention should be interpreted solely on the basis of the following claims as such claims are read in light of the disclosure.

What is claimed is:

1. A method for preventing retinal ganglion cell death, associated with glaucoma, in an animal of the mammalian species, including humans, comprising the step of administering to the ganglion optic nerve of said mammal a pharmaceutical composition which comprises as its active ingredient one or more compounds having activity for directly blocking only a reverse mode of the sodium/calcium exchanger.

2. The method according to claim 1 wherein said pharmaceutical composition comprises ((2-[2-[4-(4-nitorbenzyloxy)phenyl]ethyl]isothiourea methanesulfonte).

3. The method according to claim 1 where said pharmaceutical composition comprises cyclosporin A.

4. The method according to claim 1 or 2 wherein the composition is an ophthalmic solution adapted for administration to the eye of a mammal in the form of intracameral injection.

5. The method according to claim 3 wherein in the ophthalmic solution the concentration of the composition is in the range of approximately 0.0001 to 1 percent weight by volume.

6. A method for altering a plausible sequence of pathological events in retinal ganglion optic cells associated with glaucoma in order to prevent retinal ganglion cell death, the sequence including the pathological depolarization of retinal ganglion cells, an influx of millimolar amounts of sodium via non-inactivating sodium channels and a subsequent reversal of the sodium/calcium exchanger, mediated by both membrane depolarization and increase intracellular sodium, causing a toxic buildup of intracellular calcium, said method comprising directly blocking only a reverse mode of the sodium/calcium exchanger in retinal ganglion cells in order to prevent buildup of the calcium level in the retinal ganglions cells to a lethal level.

7. The method according to claim 6 wherein said blocking of a reverse mode of the sodium/calcium exchanger comprises administering to the eye a composition by intracameral injection.

8. The method according to claim 7 wherein said pharmaceutical composition comprises ((2-[2-[4-(4-nitorbenzyloxy)phenyl]ethyl]isothiourea methanesulfonte).

9. The method according to claim 7 wherein said pharmaceutical composition comprises cyclosporin A.

10. The method according to claim 8 or 9 wherein the ophthalmic solution the concentration of the composition is in the range of approximately 0.0001 to 1 percent weight by volume.

11. A method for maintaining normal intracellular $Na^+$ and $Ca^+$ in ganglion cells following a period of anoxia, said method comprising contacting said ganglion neuronal cells with a pharmaceutical composition for directly blocking only a reverse mode of the sodium/calcium exchanger in the retinal ganglion neuronal cells.

12. The method according to claim 11 wherein said pharmaceutical composition comprises ((2-[2-[4-(4-nitorbenzyloxy)phenyl]ethyl]isothiourea methanesulfonte).

13. The method according to claim 11 wherein said pharmaceutical composition comprises cyclosporin A.

14. The method according to claim 12 or 13 wherein the composition is an ophthalmic solution adapted for administration to the eye of a mammal in the form of intracameral injection.

15. The method according to claim 14 wherein the ophthalmic solution the concentration of the composition is in the range of approximately 0.0001 to 1 percent weight by volume.

16. A method for providing neuroprotective effect to retinal ganglion cells in the eye of a human with glaucoma which comprises the step of administering to the human eye a pharmaceutical composition which comprises as its active ingredient one or more compounds having activity for directly blocking only a reverse mode of the sodium/calcium exchanger.

17. The method according to claim 16 wherein said pharmaceutical composition comprises ((2-[2-[4-(4-nitorbenzyloxy)phenyl]ethyl]isothiourea methanesulfonte).

18. The method according to claim 16 wherein said pharmaceutical composition comprises cyclosporin A.

19. The method according to claim 17 or 18 wherein the composition is an ophthalmic solution adapted for administration to the eye of a mammal in the form of intracameral injection.

20. The method according to claim 19 wherein in the ophthalmic solution the concentration of the composition is in the range of approximately 0.0001 to 1 percent weight by volume.

* * * * *